(12) United States Patent
Hutter et al.

(10) Patent No.: US 10,137,618 B2
(45) Date of Patent: Nov. 27, 2018

(54) DEVICE FOR PRODUCING PLASTICS PARTS HAVING INSERTS

(71) Applicant: Gerresheimer Regensburg GmbH, Regensburg (DE)

(72) Inventors: Josef Hutter, Geiselhoering (DE); Michael Wiglenda, Irchenrieth (DE); Gerhard Schloegl, Pfreimd (DE)

(73) Assignee: Gerresheimer Regensburg GMBH, Regensburg (DE)

( * ) Notice: Subject to any disclaimer, the term of this patent is extended or adjusted under 35 U.S.C. 154(b) by 236 days.

(21) Appl. No.: 15/188,147

(22) Filed: Jun. 21, 2016

(65) Prior Publication Data
US 2016/0375617 A1  Dec. 29, 2016

(30) Foreign Application Priority Data

Jun. 23, 2015  (EP) .................................. 15173459

(51) Int. Cl.
*B29C 45/14*  (2006.01)
*B29C 45/33*  (2006.01)
(Continued)

(52) U.S. Cl.
CPC ......... *B29C 45/14065* (2013.01); *A61M 5/34* (2013.01); *B29C 45/03* (2013.01);
(Continued)

(58) Field of Classification Search
CPC .......... A61M 5/34; A61M 5/343; A61M 5/32; A61M 5/3293; A61M 5/3134;
(Continued)

(56) References Cited

U.S. PATENT DOCUMENTS 9,345,846 B1 *  5/2016  Rabinne .................. B29C 45/14
2012/0009816 A1  1/2012  Hiraoka et al.
(Continued)

FOREIGN PATENT DOCUMENTS

EP   2140896   1/2010
EP   2468209   6/2012
(Continued)

OTHER PUBLICATIONS

European Extended Search Report, dated Oct. 7, 2015, corresponding to European Application No. 15173459.7 (filed Jun. 23, 2015), parent of the present application, 3 pp.
(Continued)

*Primary Examiner* — Seyed Masoud Malekzadeh
*Assistant Examiner* — Lawrence D. Hohenbrink, Jr.
(74) *Attorney, Agent, or Firm* — Leydig, Voit & Mayer, Ltd.

(57) ABSTRACT

A device for producing plastics parts having at least one rod-shaped metal insert, and comprising first and second mold half elements. At least one of the mold half elements is movable along a closure direction (Z). The mold half elements together can form a closed cavity for molding a plastics part, the insert projecting at least in portions into the cavity in order to be overmolded with plastics material, and being substantially arranged between the two mold half elements in a dividing plane which comprises a longitudinal direction (X) and a width direction (Y). At least one of the mold half elements has at least one fixing means wherein the insert can be fixed in the width direction. A positioning means can be arranged at a proximal end of the insert, allowing the insert to be moved along the longitudinal direction (X) into an injection position.

17 Claims, 5 Drawing Sheets

(51) Int. Cl.
*A61M 5/34* (2006.01)
*B29C 45/03* (2006.01)
*B29C 45/27* (2006.01)
*A61M 5/32* (2006.01)
*A61M 5/31* (2006.01)
*B29L 31/00* (2006.01)
*B29K 105/20* (2006.01)
*B29K 705/00* (2006.01)

(52) U.S. Cl.
CPC .. *B29C 45/14336* (2013.01); *B29C 45/14549* (2013.01); *B29C 45/27* (2013.01); *B29C 45/33* (2013.01); *A61M 5/3134* (2013.01); *A61M 5/32* (2013.01); *A61M 5/3293* (2013.01); *A61M 5/343* (2013.01); *A61M 2207/10* (2013.01); *B29C 2045/14106* (2013.01); *B29C 2045/14122* (2013.01); *B29C 2045/14139* (2013.01); *B29C 2045/14163* (2013.01); *B29K 2105/20* (2013.01); *B29K 2705/00* (2013.01); *B29L 2031/7544* (2013.01)

(58) Field of Classification Search
CPC .............. B29C 45/14065; B29C 45/14; B29C 2045/14106; B29C 2045/14163
USPC ........................................................ 425/116
See application file for complete search history.

(56) References Cited

U.S. PATENT DOCUMENTS

2013/0138047 A1    5/2013  Takemoto et al.
2017/0014580 A1*   1/2017  Oonishi ............ B29C 45/14065

FOREIGN PATENT DOCUMENTS

EP        3127677         2/2017
WO        2012/150897    11/2012
WO        2015/033951     3/2015

OTHER PUBLICATIONS

European Examination Report, dated Oct. 19, 2017, in European patent application serial No. 15173459.7, 2 pp.

* cited by examiner

DEVICE FOR PRODUCING PLASTICS PARTS HAVING INSERTS

CROSS-REFERENCE TO RELATED APPLICATIONS

This patent application claims the benefit of priority from European application EP 15 173 459.7, filed on Jun. 23, 2015, the contents of which are incorporated herein by reference.

BACKGROUND OF THE INVENTION

The invention relates to a device for producing plastics parts having in each case at least one rod-shaped metal insert, in particular a medical puncture means, in an injection moulding process, comprising a first mould half element and a second mould half element, at least one of the mould half elements being movable along a closure direction (Z) such that in a closed position, the two mould half elements together form a closed cavity for moulding a plastics part, the insert projecting at least in portions into the cavity in order to be overmoulded with plastics material, and being substantially arranged between the two mould half elements in a mould dividing plane which comprises a longitudinal direction (X) and a width direction (Y).

Generic devices for producing plastics parts having in each case at least one rod-shaped metal insert, in particular a medical puncture means, in an injection moulding process are known from the prior art. Specifically in medical technology, very different inserts, such as needles, cannulas or the like are inserted into injection moulds in order to overmould them with plastics material in the cavity formed by the injection mould. The inserts are generally inserted into a lower mould half element of a vertical mould arrangement. However, it is also conceivable to use a horizontal mould arrangement. The plastics material is usually delivered to the cavity via one or more runners and passes into the cavity via a gate or a nozzle. After the insert has been overmoulded, the finished product, namely the plastics part having the insert, is ejected from the corresponding mould half element by an ejection apparatus and is removed from the injection mould by a removal apparatus. Usually, the mould half element comprising the nozzle is known as the injector side and the mould half element comprising the ejector is known as the ejector side.

Plastics parts having inserts specifically for medical uses, for example syringes, infusion sets, lancing aids and puncture elements of capsule inhalers, etc. are produced in this manner. Here, a very low tolerance of the needle or cannula respectively to the plastics part is often acceptable. When used on the human body in particular, inserts which are positioned outside this tolerance can cause severe pain or serious damage if a medical instrument does not function. Furthermore, faulty components of this type can damage medical instruments which make use of these components. Thus, the tolerance ranges in a production process of this type are extremely narrow, to be able to ensure the full functionality of every plastics part produced in this way. Even the smallest positional differences of an insert to be overmoulded can result in the fact that a medical plastics part cannot be used later on. Hence the requirement that the inserts which can have very small dimensions specifically in medical technology must be inserted in an extremely precise manner into the cavity of the injection mould.

Hitherto, attempts have been made to achieve these low tolerances by precise handling robots. However, such exact handling systems are very expensive and, from a performance point of view, are almost incapable of maintaining the required tolerances. Furthermore, there is a very high risk that after the inserts have been positioned correctly, the position thereof will change again because the insert cannot be fixed satisfactorily between the positioning procedure and the injection moulding process. Alternatively, inserts are often pushed onto a stop. However, since the above-mentioned articles such as needles and cannulas have very sensitive ground surfaces which are extremely critical for the function of a medical instrument, this is not feasible here. Thus, the distal ground surface would be destroyed when impacting a stop as it would by a slide which is to be pushed against this distal end.

Thus, the object of the present invention is to provide a device for producing plastics parts having in each case at least one rod-shaped metal insert, in particular a medical puncture means, in an injection moulding process, which device avoids the above-mentioned problems.

SUMMARY OF THE INVENTION

This object is achieved by a device for producing plastics parts having in each case at least one rod-shaped metal insert, in particular a medical puncture means, in an injection moulding process, comprising a first mould half element and a second mould half element, at least one of the mould half elements being movable in a closure direction (Z) such that in a closed position, the two mould half elements together form a closed cavity for moulding a plastics part, the insert projecting at least in portions into the cavity in order to be overmoulded with plastics material, and being substantially arranged between the two mould half elements in a mould dividing plane which comprises a longitudinal direction (X) and a width direction (Y). The device is characterized in that at least one of the mould half elements has at least one fixing means, by means of which the insert can be fixed in the width direction (Y), and in that a positioning means can be arranged at a proximal end of the insert, by which the insert, which is fixed in the width direction (Y), can be moved along the longitudinal direction (X) into an injection position.

Thus, in the device according to the invention, the inserts are preferably inserted into the mould in a very roughly defined position. In this respect, this first position preferably differs considerably from the desired axial injection position. The insert can then be moved at its proximal end to the injection position by the positioning means. Here, "a proximal end" of the insert is understood as meaning the end without a ground surface. Moreover, since the insert is fixed in a width direction (Y), it can easily be positioned very precisely in the cavity. A complicated handling robot is not required, neither does the insert have to strike against a stop at its distal end, i.e. at its end which has a ground surface.

The positioning means preferably has a slide core which is substantially arranged in the mould dividing plane. Furthermore, this slide core has an end face which can contact an end face on the proximal end of the insert. As a result, a translational force can be transferred to the insert and the insert can be moved along a longitudinal direction (X) into the injection position. This end face is preferably a planar surface. However, other configurations of the end face are conceivable. In particular, if the end face, which is to be contacted, on the proximal end of the insert is not a planar surface, it can be advantageous for the end face of the slide core to have a different shape. For example, shapes are conceivable which are complementary to the end face of the insert or which are configured as a different receptacle. Furthermore, the slide core is preferably formed in the shape of a rod and preferably has a greater diameter than the insert. In a particularly preferred manner, the diameter of the slide core corresponds to the diameter of the insert.

According to an advantageous aspect of the invention, the positioning means comprises an end piece on which the slide core is arranged. It is conceivable that the end piece and the slide core consist of the same material, for example of a heat-resistant plastics material or a metal. However, it would also be conceivable for the end piece and the slide core to consist of different materials. Furthermore, it would be conceivable to arrange the slide core on the end piece such that the slide core or the end piece can be changed. In a particularly preferred manner, the slide core has a nail-like end portion having a head. This end portion is preferably embedded in the end piece.

The mould half elements preferably have receptacles, portions of which are complementary to the end piece. When the mould half elements are in the closed position, the end piece of the positioning means is preferably received in the receptacles. Thus, in the closed position, the mould half elements advantageously encompass the end piece at least in part.

According to a further preferred embodiment, at least one of the mould halves comprises an actuating surface and the end piece comprises at least one ramp surface. The actuating surface and the ramp surface respectively are preferably configured as inclined surfaces. In this respect, the two inclined surfaces preferably form an identical angle ($\alpha$, $\beta$) relative to a perpendicular. This angle ($\alpha$, $\beta$) is preferably between 10° and 60°. During a closure movement of the mould half elements, the end piece can preferably be moved from a starting position into an end position due to a sliding movement of the at least one actuating surface of the mould halves on the at least one ramp surface of the end piece. Accordingly, the closure movement of the mould half elements causes the positioning means to move. This is a particularly simple configuration of a slide mechanism for the slide core. However, other slide mechanisms are also conceivable, for example the slide core could be moved into the end position hydraulically, pneumatically, by spring force or by a transmission.

The device preferably also comprises a resetting apparatus, by which the end piece is movable from the end position into the starting position during an opening movement of the mould half elements. A resetting apparatus of this type could be a spring element, for example. However, a hydraulic, pneumatic or another mechanical positioning member would also be conceivable to move the end piece or the positioning means respectively back into the starting position. It would also be conceivable for guide elements for the end piece to be arranged in one of the two mould half elements. These could be configured, for example, on one of the mould half elements by at least one recess, extending along the longitudinal direction (X), in the end piece, which recess is complementary to at least one guide projection. It would also be conceivable for at least one of the mould half elements to have said at least one recess and for the at least one guide projection to be arranged on the end piece.

According to a preferred embodiment, the injection position of the insert is defined by the end position of the end piece, in which position an end face of the end piece contacts the particular end face of the receptacles of the mould halves and fixes the length of the slide core. Thus, the insert to be overmoulded is firstly introduced between the mould half elements, this first position preferably differing considerably from the desired axial injection position. The insert is preferably pushed by the slide core into the required injection position. Thus, the insert can be positioned very precisely. If the injection position has to be adjusted because, for example, a shorter or longer insert is to be used, all that needs to be done is to change the positioning means or the slide core respectively.

According to a further preferred embodiment, the first mould half element has a first fixing means and the second mould half element has a second fixing means. These fixing means preferably run into the mould dividing plane and are more preferably arranged outside the cavity. These two fixing means advantageously fix the insert in the width direction (Y) of the mould half elements. Thus, the insert is movable only along the longitudinal direction (X).

The first fixing means preferably comprises a magnetic portion for fixing the insert, the magnetic portion terminating in a planar manner with a surface of the first mould half element. It would also be conceivable for a different charging effect to be used for fixing the insert instead of the magnetic effect.

The second fixing means preferably comprises at least one centring pin. This centring pin is preferably pressurised by a spring element so that it projects in portions into the mould dividing plane when the mould half elements are in an open position. When the mould half elements are in the closed position, the centring pin is movable, against the spring force, out of the mould dividing plane counter to the closure direction (Z). The spring element preferably comprises a coil spring. However, other types of spring are also conceivable, such as for example leg springs or torsion springs. It would also be conceivable to form the spring element as an elastomer.

In a particularly preferred manner, the centring pin has centring surfaces on its end face for centring the insert with respect to the width direction (Y). These centring surfaces are preferably circular arc-shaped or conical. However, other shapes are also conceivable, for example shapes which are partly complementary to the insert. If the insert is held just by using a magnetic fixing (or using other charging effects respectively), the insert may jump or may shift undesirably when it is moved by the positioning means in the longitudinal direction (X). This is prevented very effectively by an additional centring pin.

According to a preferred embodiment, the device contains at least one runner which leads to the cavity and is guided in part in the second mould half element. Since the insert and thereby also the corresponding positioning means, in particular the slide core and the slide mechanism, are preferably located approximately in the mould dividing plane, this can result in the fact that, in the case of fuller moulds in particular, the slide mechanism could interfere with a runner. To prevent this from happening, the runner is advantageously guided in part in the injector side of the mould.

According to a further preferred embodiment, a preferably trapezoidal slide core cover is arranged in the region of the at least one runner between the slide core and the runner. This is to prevent the slide mechanism from being soiled by the sprue or to prevent particles from even passing from the sprue into the cavity.

The first and the second mould half elements are preferably arranged horizontally, the second mould half element being arranged above the first mould half element in the vertical closure direction (Z).

Further advantages, aims and characteristics of the present invention are described by means of the following description of the accompanying figures. Similar components can have the same reference signs in the different embodiments.

DETAILED DESCRIPTION OF THE INVENTION

Figure 1:
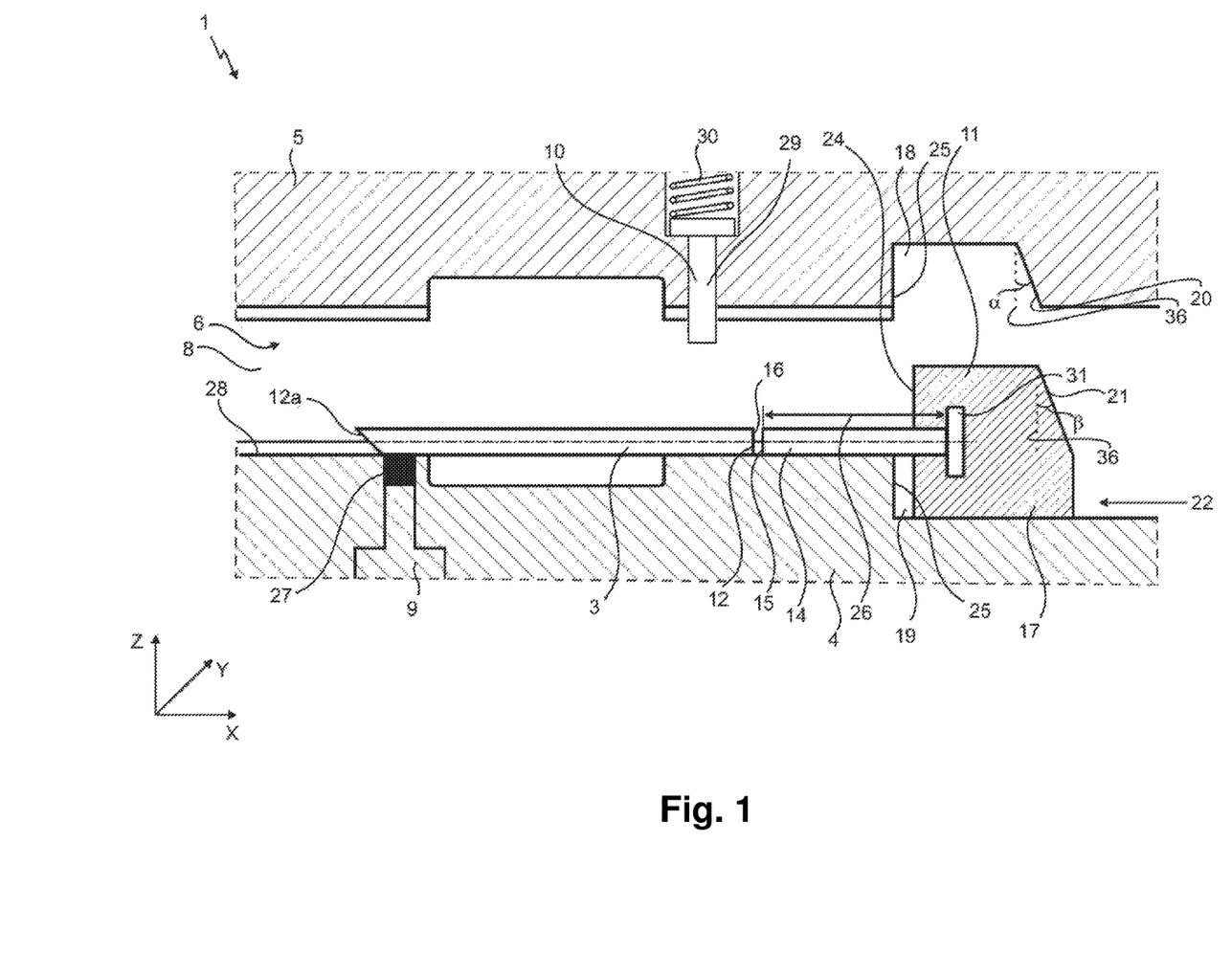
FIG. 1 shows a sectional view of a device, in an open position, for producing plastics parts having in each case at least one insert.
Figure 2:
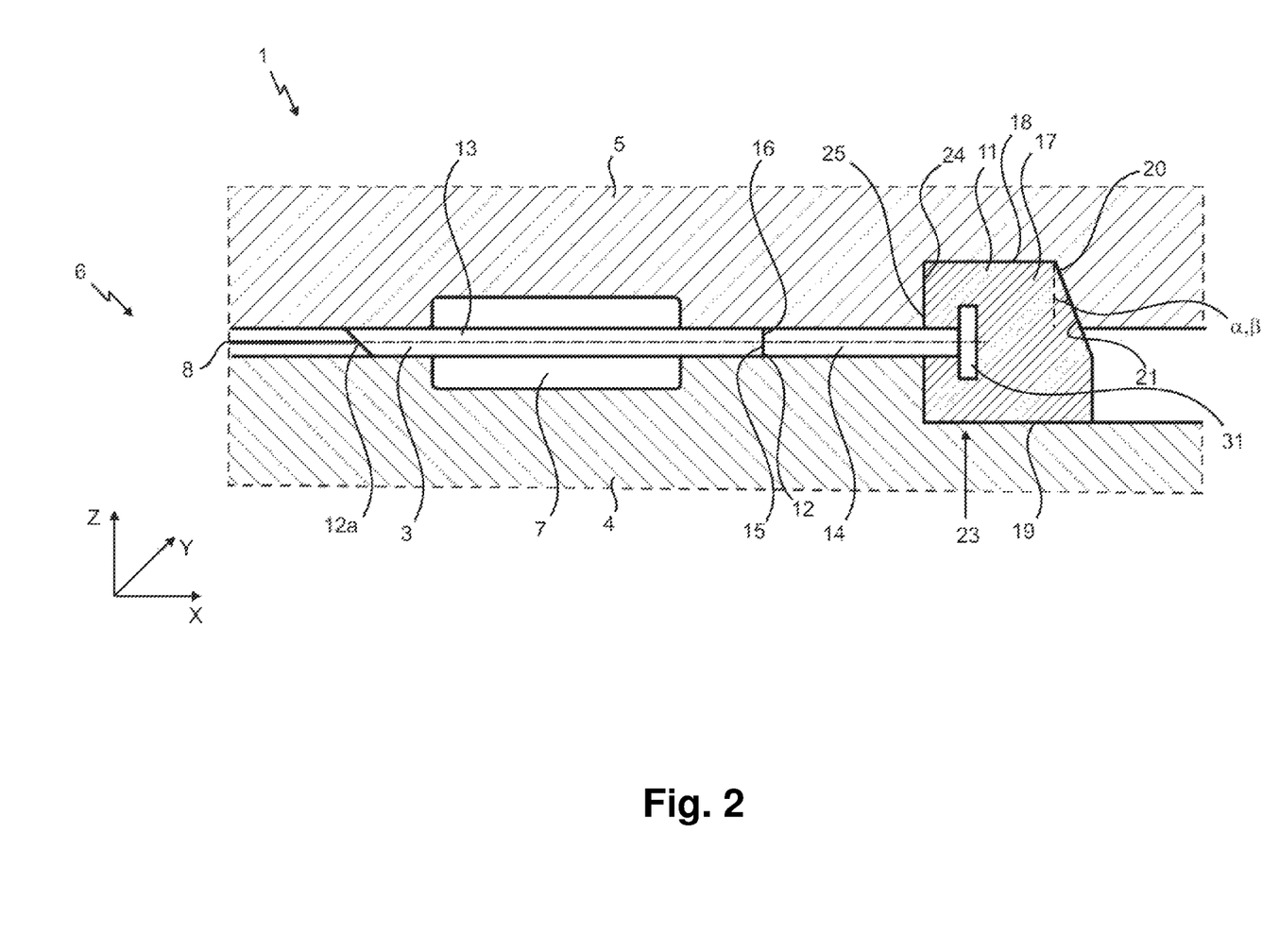
FIG. 2 shows a sectional view of a device, in a closed position, for producing plastics parts having in each case at least one insert.

FIGS. 1 and 2 show a device (1) for producing plastics parts (2) having in each case at least one rod-shaped metal insert (3), in particular a medical puncture means, in an injection moulding process. In this respect, FIG. 1 shows an open position (6a) and FIG. 2 shows a closed position (6b) of the device.

The device (1) comprises a first mould half element (4) and a second mould half element (5). At least one of the mould half elements (4, 5) can be moved along a closure direction (Z) such that, in a closed position (6b), the two mould half elements (4, 5) together form a closed cavity (7) for moulding a plastics part (2). In this respect, the two mould half elements (4, 5) can extend in a horizontal direction, in which case the closure direction (Z) would then be a vertical direction. The second mould half element (5) would thus be arranged above the first mould half element (4) in the vertical closure direction (Z). However, it would also be possible for the two mould half elements (4, 5) to extend in a vertical direction, in which case the closure direction (Z) would then be a horizontal direction.

Figure 5:
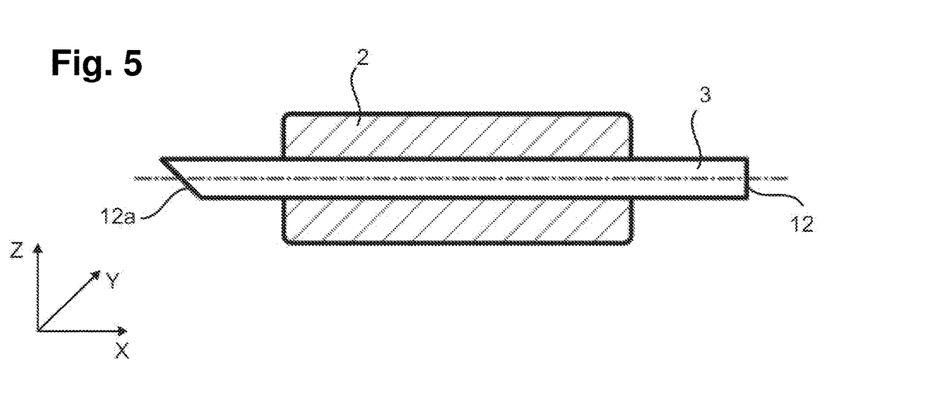
FIG. 5 shows a sectional view of a plastics part having an insert.

The insert (3) for overmoulding with plastics material projects at least in portions into the cavity (7) and is substantially arranged between the two mould half elements (4, 5) in a mould dividing plane (8). This mould dividing plane (8) comprises a longitudinal direction (X) and a width direction (Y). In this embodiment, the cavity (7) is cylindrical and the insert (3) projects beyond the cavity (7) on both sides in the longitudinal direction (X). The insert (3) has a proximal end (12) and a distal end (12a), the distal end (12a) being provided with a ground surface. A plastics part (2) which is shaped by way of example so as to have the cavity (7) and which has a rod-shaped metal insert (3) is shown in FIG. 5.

The two mould half elements (4, 5) further each have a fixing means (9, 10), by means of which the insert (3) can be fixed in the width direction (Y). Furthermore, a positioning means (11) can be arranged at a proximal end (12) of the insert (3), by which positioning means the insert (3), fixed in the width direction (Y), can be moved along the longitudinal direction (X) into an injection position (13). The positioning means (11) comprises a slide core (14) which is substantially arranged in the mould dividing plane (8). This slide core (14) in turn has an end face (15) which can contact an end face (16) on the proximal end (12) of the insert (3). Consequently, a translational force can be transferred to the insert (3), as a result of which the insert (3) can be moved along a longitudinal direction (X) into the injection position (13).

Furthermore, the positioning means (11) comprises an end piece (17) on which the slide core (14) is arranged. The mould half elements (4, 5) each have a receptacle (18, 19), portions of which are complementary to the end piece (17). Thus, when the mould half elements (4, 5) are in the closed position (6b) shown in FIG. 2, the end piece (17) has been received in the receptacles (18, 19).

The slide core (14) is formed in the shape of a rod and has a nail-like end portion (31) having a head. In this respect, this nail-like end portion (31) is embedded in the end piece (17). The receptacles (18, 19) of the mould half elements (4, 5) are configured such that the slide core (14) can be moved in the mould dividing plane (8). In particular, the receptacles (18, 19) have the same height in the closure direction (Z), as a result of which the slide core (14) which is movable in the mould dividing plane (8) is arranged centrally on the end piece (17).

Furthermore, the second mould half (5) comprises an actuating surface (20) and the end piece (17) has a ramp surface (21). The actuating surface (20) and the ramp surface (21) respectively are formed as inclined surfaces. In this respect, the two inclined surfaces preferably form an identical angle ($\alpha$, $\beta$) with respect to a perpendicular (36). This angle ($\alpha$, $\beta$) is preferably between 10° and 60°. Thus, during a closure movement of the mould half elements (4, 5), the end piece (17) can be moved from a starting position (22) into an end position (23) as a result of the actuating surface (20) sliding on the ramp surface (21). The end piece or the positioning means respectively is thus actuated mechanically by the second mould half element (5).

Figure 7:
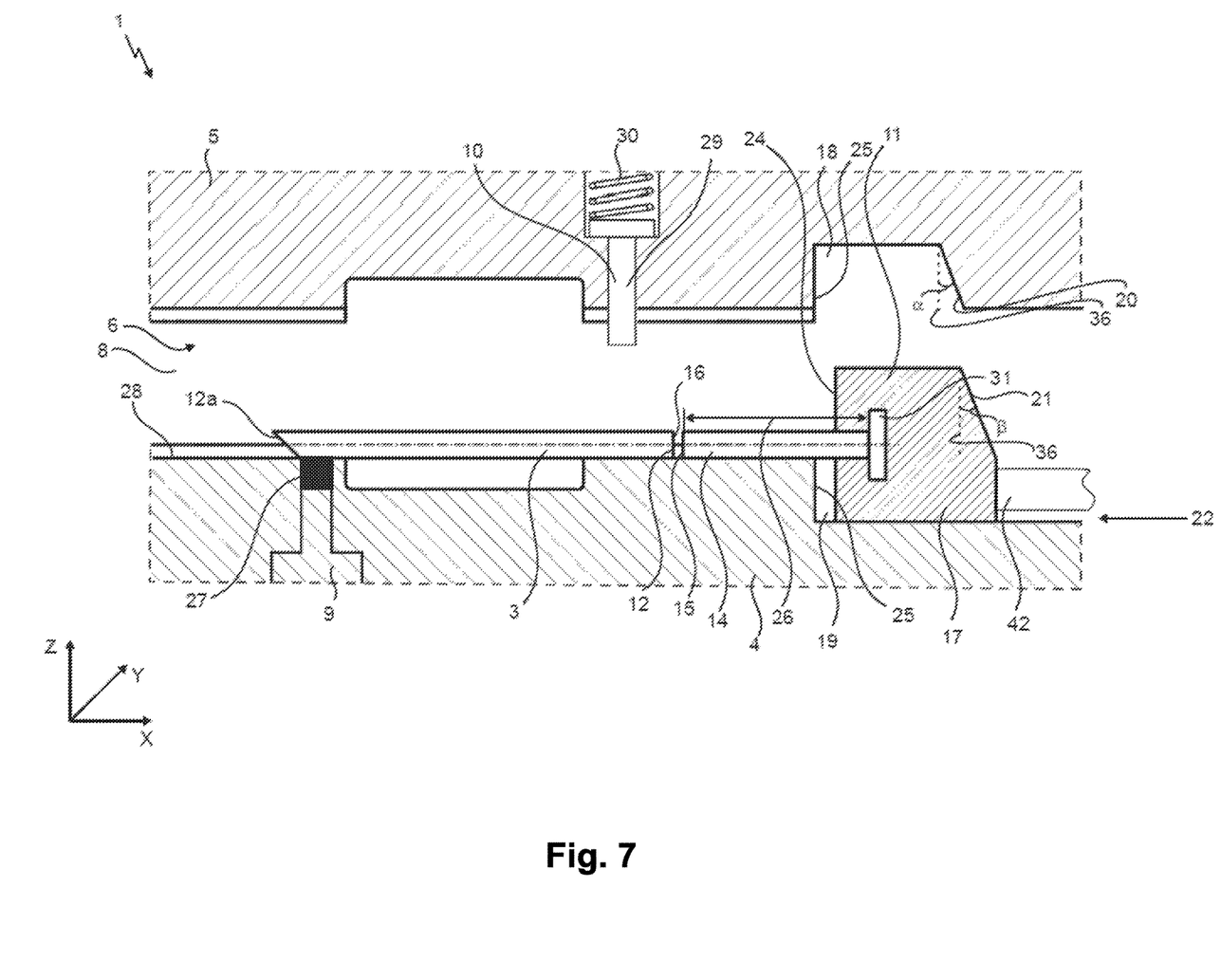
FIG. 7 shows a sectional view of a device for producing plastics parts, where the device further comprises a resetting apparatus.

In this end position (23), an end face (24) of the end piece (17) contacts the particular end face (25) of the receptacles (18, 19) of the mould half elements (4, 5). The injection position (13) of the insert (3) is thus fixed by the end position (23) of the end piece (17) and by the length (26) of the slide core (14). If a different injection position (13) of the insert (3) is desired, the positioning means or the slide core respectively can be changed accordingly. Furthermore, it is an advantage for the device (1) to comprise a resetting apparatus (42), by means of which the end piece (17) can be moved from the end position (23) into the starting position (22) during an opening movement of the mould half elements (4, 5). A resetting apparatus of this type is shown in FIG. 7.

Furthermore, the first mould half element (4) and the second mould half element (5) have a first fixing means (9) and a second fixing means (10). The two fixing means (9, 10) run into the mould dividing plane (8) and are arranged outside the cavity (7). Thus, the insert (3) is fixed by the two fixing means (10) in the width direction (Y) of the mould half elements (4, 5).

Figure 3:
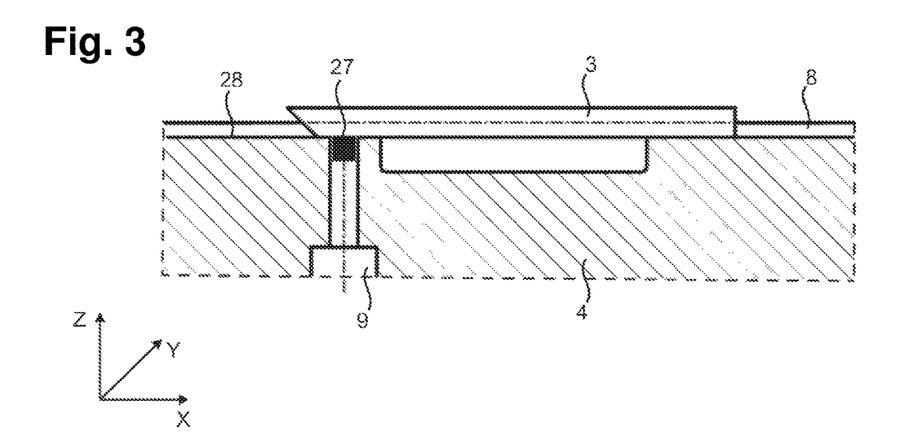
FIG. 3 shows a sectional view of a fixing means in the device for producing plastics parts having in each case at least one insert.

In addition, the first fixing means (9) comprises a magnetic portion (27). In this respect, the magnetic portion (27) terminates in a planar manner with a surface (28) of the first mould half element (4). The metal inserts (3) can thus be fixed by the magnetic force of the portion (27). A detailed view of the first fixing means (9) is shown in FIG. 3.

The second fixing means (10) comprises a centring pin (29) for fixing and centring the insert (3). The second fixing means (10) is shown in detail in FIG. 4. The centring pin is arranged such that it can move in a channel (37) in the second mould half element (5). The channel opens into a spring chamber (38), the diameter of which is greater than that of the channel. Arranged in the spring chamber (38) is a plunger-like plate (39) which is pressurised by a spring element (30) arranged in the spring chamber. The spring element (30) is configured as a coil spring which has a stroke in the closure direction (Z). The central axis of the coil spring is located on a central axis (41) of the centring pin (29). The centring pin (29) is connected on the back to the plunger-like plate (39) and is thereby pressurised on the back by the spring element (30). In the open position (6a) of the mould half elements (4, 5), the plunger-like plate (39) rests against a lower inner wall (40) of the spring chamber (38) due to the spring force of the spring element (30). Consequently, portions of the centring pin (29) project into the mould dividing plane (8) due to the spring force of the spring element (30). Due to the plunger-like plate (39) resting against the lower inner wall (40) of the spring chamber (38), a maximum length of the centring pin (29), which projects into the mould dividing plane (8), is fixed accordingly. When the centring pin (29) contacts the insert (3) during a closure movement of the mould half elements (4, 5), the centring pin is thereafter moved into the channel (37) against the closure direction (Z) during a further closure movement. As a result, the plunger-like plate (39) is in turn moved and the spring element (30) is tensioned.

Figure 4:
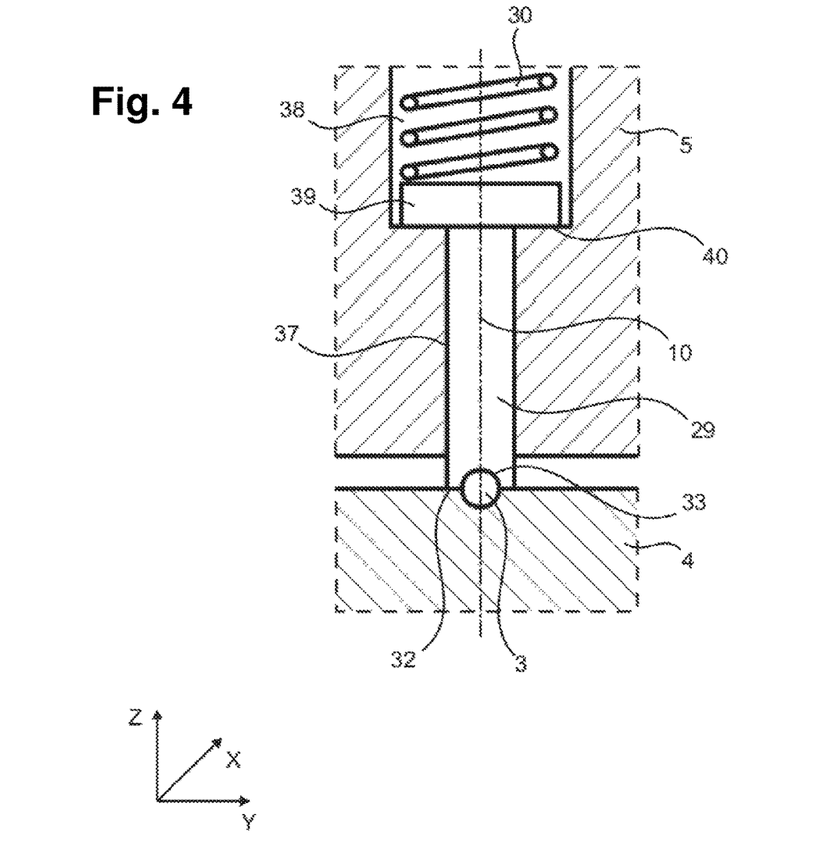
FIG. 4 shows a sectional view of a fixing means in the device for producing plastics parts having in each case at least one insert.

The centring pin (29) further has centring surfaces (33) on its end face (32) for centring the insert (3) in relation to the width direction (Y). The inserts (3) usually have a circular cross section. In this embodiment, centring surfaces (33) are in the shape of a circular arc, by which the insert is centred and fixed in the width direction (Z).

Figure 6:
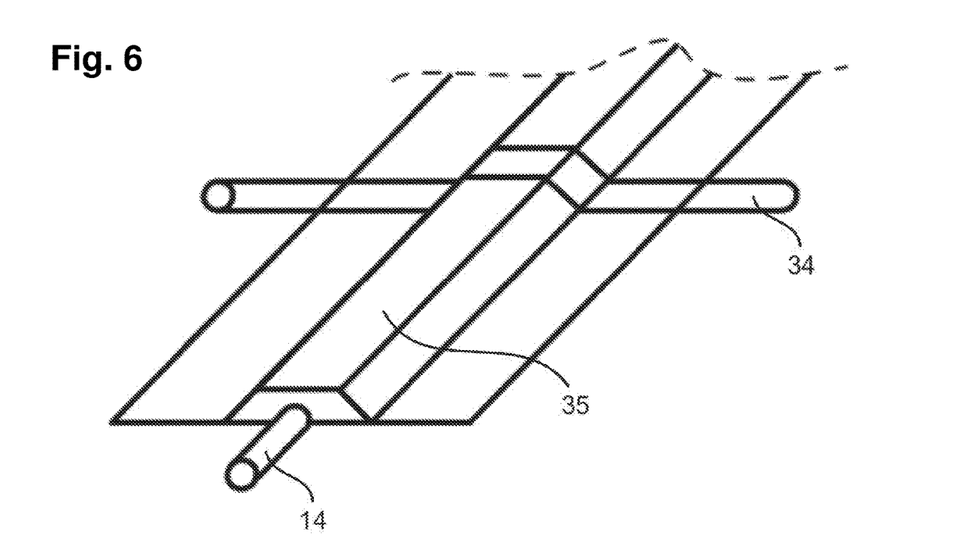
FIG. 6 shows an isometric view of a slide core having a slide core cover.

The device (1) contains at least one runner (34) which leads to the cavity (7) and is guided at least in part in the second mould half element (5). FIG. 6 shows the slide core (14). In the region of the runner (34), a trapezoidal slide core cover (35) is arranged between the slide core (14) and the runner (34). This is to prevent the slide mechanism from becoming soiled by the sprue or to even prevent particles from passing from the sprue into the cavity (7).

In the following, a sequence is to be described for the production of a plastics part (2) having in each case at least one rod-shaped metal insert (3) using the above-described device (1). The mould half elements (4, 5) are initially in an open position (12a). The inserts (3) are inserted between the mould half elements (4, 5) in a very roughly defined position, the proximal end (12) (the end without the ground surface) of the insert (3) being directed towards the slide core (14). The insert (3) is initially fixed only by the first fixing means (9) by the magnetic force of the magnetic portion (27). In this respect, this first position of the insert (3) differs considerably from the required axial injection position (13). This open position (12a) of the mould half elements (4, 5) is shown in FIG. 1. The end face (15) of the slide core (14) does not contact the end face (16) on the proximal end (12) of the insert (3) in this case. The end piece (17) is in a starting position (22). During a closure movement, the mould half elements (4, 5) move towards each other. The centring pin (29) which projects into the mould dividing plane now comes into contact with the insert (3). The insert (3) is centred in the width direction (Y) by the centring surfaces (33) on the end face (32) of the centring pin (29). This very effectively prevents a jumping movement, which can happen particularly when a purely magnetic fixing is used, or prevents an undesirable shift of the needle. At the same time, the actuating surface (20) of the second mould half element (5) and the ramp surface (21) of the end piece (17) contact one another. Due to a sliding movement of the actuating surface (20) on the ramp surface (21), the end piece is moved from its starting position (22).

Consequently, the slide core (14) is also moved towards the insert (3). Thereafter, when the end face (15) of the slide core (14) and the end face (16) on the proximal end (12) of the insert (3) contact one another, a translational force is transferred to the insert (3) and the insert (3) is moved along the longitudinal direction (X). In a closed position (6b), shown in FIG. 2, the end piece (17) is in its end position (23) in which the end face (24) of the end piece (17) rests against the respective end faces (25) of the receptacles (18, 19) of the mould half elements (4, 5). The mould half elements (4, 5) together form a closed cavity (7) for moulding a plastics part (2). The insert (3) is in the injection position (13). In this position, said insert is delimited in the longitudinal direction (X) by the slide core (14) and is fixed and centred in the width direction by the first and second fixing means. Very accurate positioning of the insert (3) is ensured thereby. The injection procedure then takes place in this injection position (13). Thereafter, the mould half elements (4, 5) are opened and the finished plastics part (2) having at least one rod-shaped metal insert (3) can be removed.

All the features which are disclosed in the application documents are claimed as being essential to the invention, provided that, individually or combined, they are novel over the prior art.

Having now fully described the present invention in some detail by way of illustration and examples for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Headings are used herein for convenience only.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. In the disclosure and the claims, "and/or" means additionally or alternatively. Moreover, any use of a term in the singular also encompasses plural forms.

All publications referred to herein are incorporated herein to the extent not inconsistent herewith. Some references provided herein are incorporated by reference to provide details of additional uses of the invention. All patents and publications mentioned in the specification are indicative of the levels of skill of those skilled in the art to which the invention pertains. References cited herein are incorporated by reference herein in their entirety to indicate the state of the art as of their filing date and it is intended that this information can be employed herein, if needed, to exclude specific embodiments that are in the prior art.

LIST OF REFERENCE SIGNS 1 device for producing plastics parts
2 plastics part
3 insert
3a first mould half element
3b second mould half element
4 distal end of injection body
5 cylindrical end piece
6a open position
6b closed position
7 cavity
8 mould dividing plane
9 first fixing means
10 second fixing means
11 positioning means
12 proximal end of insert
12a distal end of insert
13 injection position
14 slide core
15 end face of slide core
16 end face of insert
17 end piece
18 receptacle of first mould half element
19 receptacle of second mould half element
20 actuating surface
21 ramp surface
22 starting position of end piece
23 end position of end piece
24 end face of end piece
25 respective end face of receptacles
26 length of slide core
27 magnetic portion of first fixing means
28 surface of first mould half element
29 centring pin
30 spring element
31 nail-like end portion of slide core
32 end face of centring pin
33 centring surfaces
34 runner
35 slide core cover
36 perpendicular
37 channel
38 spring chamber
39 plunger-like plate
40 lower inner wall of spring chamber
41 central axis of centring pin
X longitudinal direction
Y width direction
Z closure direction

We claim:

1. A device for producing plastics parts, comprising in each case at least one rod-shaped metal insert, which has a proximal end and a distal end having a ground surface, in an injection moulding process, comprising a first mould half element and a second mould half element, at least one of the mould half elements being movable along a closure direction such that in a closed position, the mould half elements together form a closed cavity for moulding a plastics part, the insert projecting at least in portions into the cavity in order to be overmoulded with plastics material and being substantially arranged between the mould half elements in a mould dividing plane which comprises a longitudinal direction and a width direction, wherein at least one of the mould half elements has at least one fixing means, by which the insert can be fixed in the width direction, and in that a positioning means is able to be arranged at the proximal end of the insert, by which the insert, which is fixed in the width direction, is able to be moved along the longitudinal direction into an injection position,
wherein the positioning means comprises an end piece on which a slide core is arranged, wherein at least one of the mould half elements comprises an actuating surface and the end piece comprises at least one ramp surface, the end piece being movable, during a closure movement of the mould half elements, from a starting position into an end position due to a sliding movement of the at least one actuating surface on the at least one ramp surface.

2. The device according to claim 1, wherein the positioning means comprises a slide core which is substantially arranged in the mould dividing plane, the slide core comprising an end face which is able to contact an end face on the proximal end of the insert, as a result of which a translational force is able to be transferred to the insert and the insert is able to be moved in the longitudinal direction into the injection position.

3. The device according to claim 1, wherein the mould half elements having receptacles, portions of which are complementary to the end piece and the end piece being received in the receptacles when the mould half elements are in the closed position.

4. The device according to claim 3, wherein the device comprises a resetting apparatus, by means of which the end piece is movable from an end position into a starting position during an opening movement of the mould half elements.

5. The device according to claim 1, wherein the first mould half element comprises a first fixing means and the second mould half element comprises a second fixing means, said first and second fixing means running into the mould dividing plane, being arranged outside the cavity and fixing the insert in the width direction of the mould half elements.

6. The device according to claim 5, wherein the first fixing means comprises a magnetic portion for fixing the insert, the magnetic portion terminating in a planar manner with a surface of the first mould half element.

7. The device according to claim 5, wherein the second fixing means comprises at least one centring pin for fixing and centring the insert, the centring pin being pressurised by a spring element so that when the mould half elements are in an open position, the centring pin projects in portions into the mould dividing plane and is movable, against a spring force, out of the mould dividing plane counter to the closure direction when the mould half elements are in the closed position.

8. The device according to claim 7, wherein the centring pin has centring surfaces on an end face for centring the insert with respect to the width direction.

9. The device according to claim 1, wherein the device contains at least one runner which leads to the cavity and which is guided at least in part in the second mould half element.

10. The device according to claim 9, wherein a trapezoidal slide core cover is arranged in the region of the at least one runner between the slide core and the runner.

11. The device according to claim 1, wherein the first mould half element and the second mould half element are arranged horizontally, the second mould half element being arranged above the first mould half element in a vertical closure direction.

12. A device for producing plastics parts, comprising in each case at least one rod-shaped metal insert, which has a proximal end and a distal end having a ground surface, in an injection moulding process, comprising a first mould half element and a second mould half element, at least one of the mould half elements being movable along a closure direction such that in a closed position, the mould half elements together form a closed cavity for moulding a plastics part, the insert projecting at least in portions into the cavity in order to be overmoulded with plastics material and being substantially arranged between the mould half elements in a mould dividing plane which comprises a longitudinal direction and a width direction, wherein at least one of the mould half elements has at least one fixing means, by which the insert can be fixed in the width direction, and in that a positioning means is able to be arranged at the proximal end of the insert, by which the insert, which is fixed in the width direction, is able to be moved along the longitudinal direction into an injection position, wherein the first mould half element comprises a first fixing means and the second mould half element comprises a second fixing means, said first and second fixing means running into the mould dividing plane, being arranged outside the cavity and fixing the insert in the width direction of the mould half elements, wherein the first fixing means comprises a magnetic portion for fixing the insert, the magnetic portion terminating in a planar manner with a surface of the first mould half element.

13. The device according to claim 3, wherein the injection position of the insert is ascertained by the end position of the end piece, in which position an end face of the end piece contacts respective end faces of the receptacles of the mould half elements, and by a length of a slide core.

14. The device according to claim 12, wherein the second fixing means comprises at least one centring pin for fixing and centring the insert, the centring pin being pressurised by a spring element so that when the mould half elements are in an open position, the centring pin projects in portions into the mould dividing plane and is movable, against the spring force, out of the mould dividing plane counter to the closure direction when the mould half elements are in the closed position.

15. The device according to claim 12, wherein the centring pin has centring surfaces on an end face for centring the insert with respect to the width direction.

16. A device for producing plastics parts, comprising in each case at least one rod-shaped metal insert, which has a proximal end and a distal end having a ground surface, in an injection moulding process, comprising a first mould half element and a second mould half element, at least one of the mould half elements being movable along a closure direction such that in a closed position, the mould half elements together form a closed cavity for moulding a plastics part, the insert projecting at least in portions into the cavity in order to be overmoulded with plastics material and being substantially arranged between the mould half elements in a mould dividing plane which comprises a longitudinal direction and a width direction, wherein the first mould half element comprises a first fixing means and the second mould half element comprises a second fixing means, the said first and second fixing means running into the mould dividing plane, being arranged outside the cavity and fixing the insert in the width direction of the mould half elements, and in that a positioning means is able to be arranged at the proximal end of the insert, by which the insert, which is fixed in the width direction, is able to be moved along the longitudinal direction into an injection position, wherein the second fixing means comprises at least one centring pin for fixing and centring the insert, the centring pin being pressurised by a spring element so that when the mould half elements are in an open position, the centring pin projects in portion into the mould dividing plane and is movable, against spring force, out of the mould dividing plane counter to the closure direction when the mould half elements are in the closed position.

17. The device according to claim 16, wherein the centring pin has centring surfaces on an end face for centring the insert with respect to the width direction.

\* \* \* \* \*